(12) United States Patent
Fujita et al.

(10) Patent No.: US 11,830,611 B2
(45) Date of Patent: Nov. 28, 2023

(54) DEVICE MANAGEMENT APPARATUS, DEVICE MANAGEMENT SYSTEM, AND DEVICE MANAGEMENT METHOD

(71) Applicant: Canon Medical Systems Corporation, Otawara (JP)

(72) Inventors: Fuminori Fujita, Nasushiobara (JP); Akihiro Koga, Tokyo (JP); Atsuko Sugiyama, Nasushiobara (JP); Junko Shibata, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 273 days.

(21) Appl. No.: 17/111,854

(22) Filed: Dec. 4, 2020

(65) Prior Publication Data

US 2021/0174951 A1 Jun. 10, 2021

(30) Foreign Application Priority Data

Dec. 6, 2019 (JP) .................................. 2019-221460

(51) Int. Cl.
*G16H 40/40* (2018.01)
*G06N 20/00* (2019.01)
*G05B 23/02* (2006.01)
*G16H 40/20* (2018.01)

(52) U.S. Cl.
CPC ......... *G16H 40/40* (2018.01); *G05B 23/0254* (2013.01); *G06N 20/00* (2019.01); *G16H 40/20* (2018.01)

(58) Field of Classification Search
CPC ........ G16H 40/40; G16H 40/20; G16H 40/60; G05B 23/0254; G05B 23/0297; G06N 20/00

See application file for complete search history.

(56) References Cited

U.S. PATENT DOCUMENTS

| | | | | |
|---|---|---|---|---|
| 9,460,316 | B2 * | 10/2016 | Tanamoto | G11C 11/16 |
| 9,842,302 | B2 * | 12/2017 | Bates | G05B 23/024 |
| 10,555,093 | B2 * | 2/2020 | Goorevich | H04R 25/30 |
| 10,896,114 | B2 * | 1/2021 | Savanur | G06N 3/04 |
| 10,948,906 | B2 * | 3/2021 | Marakkannu | G05B 23/0283 |

(Continued)

FOREIGN PATENT DOCUMENTS

| | | |
|---|---|---|
| JP | 2003-50718 A | 2/2003 |
| JP | 2006-135412 A | 5/2006 |

(Continued)

OTHER PUBLICATIONS

Office Action dated Jun. 26, 2023, issued in corresponding Chinese patent application No. 202011404724.4.

(Continued)

*Primary Examiner* — Mohammad K Islam
(74) *Attorney, Agent, or Firm* — Oblon, McClelland, Maier & Neustadt, L.L.P.

(57) ABSTRACT

According to one embodiment, a device management apparatus includes processing circuitry. The processing circuitry acquires information indicating occurrence of a first failure prediction of a first device. The processing circuitry adjusts detection sensitivity of a second failure prediction of a second device relating to the information based on relevance between the first device and the second device. The second device is different from the first device.

9 Claims, 10 Drawing Sheets

(56) References Cited

U.S. PATENT DOCUMENTS

| | | | |
|---|---|---|---|
| 2012/0296606 A1* | 11/2012 | Hamzaoui | G05B 19/401 |
| | | | 702/184 |
| 2018/0239345 A1 | 8/2018 | Noda | |
| 2018/0351840 A1* | 12/2018 | Kondo | H04L 41/147 |
| 2021/0021713 A1* | 1/2021 | Choi | H04L 12/66 |

FOREIGN PATENT DOCUMENTS

| | | |
|---|---|---|
| JP | 2006-349428 A | 12/2006 |
| JP | 2017-33472 A | 2/2017 |
| JP | 2018-033037 A | 3/2018 |
| JP | 2019-159730 A | 9/2019 |
| WO | 2019/177251 A1 | 1/2021 |

OTHER PUBLICATIONS

Office Action dated Aug. 1, 2023, issued in corresponding Japanese patent application No. 2019-221460.

\* cited by examiner

| Failure estimation portion | Extraction item | | | |
|---|---|---|---|---|
| X-ray tube | Production lot | Tube current | Filament current | Gantry temperature |
| Portion A | Portion | | | |
| Portion AA | Model number | | | |

| Failure estimation portion | Necessity of forwarding |
|---|---|
| Portion B | Necessary |
| Portion BB | Necessary |
| Portion BBB | Unnecessary |

FIG. 4

| Estimation cause of failure estimation portion | Necessity of forwarding |
|---|---|
| Heated ultrasound probe | Necessary |
| Defective element of ultrasound probe | Necessary |
| Cable breakage of ultrasound probe | Unnecessary |

FIG. 5

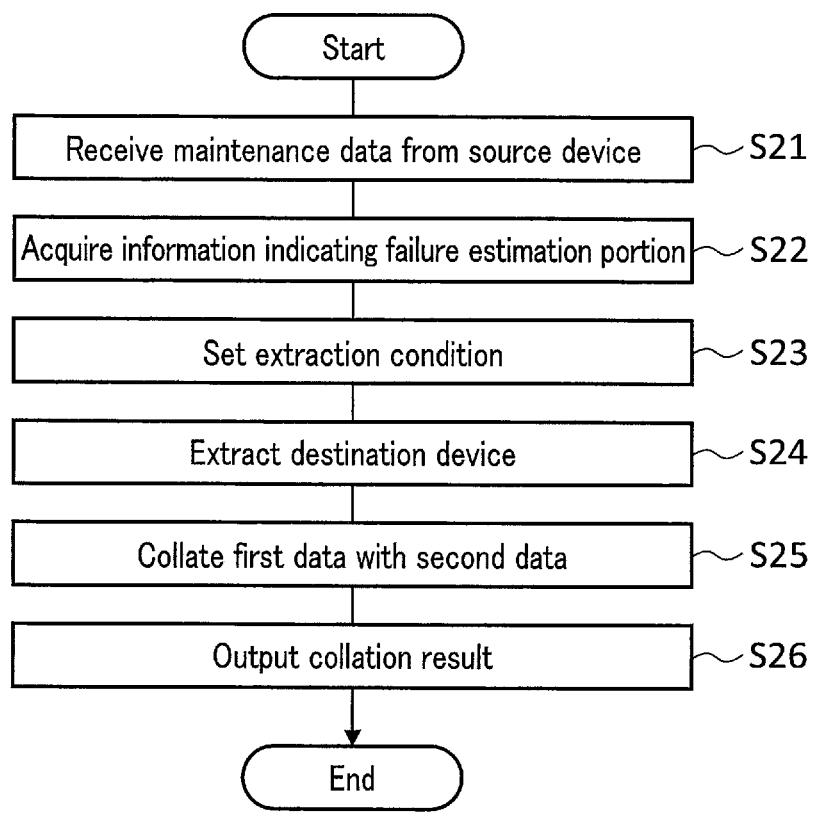
F I G. 11

DEVICE MANAGEMENT APPARATUS, DEVICE MANAGEMENT SYSTEM, AND DEVICE MANAGEMENT METHOD

CROSS-REFERENCE TO RELATED APPLICATIONS

This application is based upon and claims the benefit of priority from the prior Japanese Patent Application No. 2019-221460, filed Dec. 6, 2019, the entire contents of which are incorporated herein by reference.

FIELD

Embodiments described herein relate generally to a device management apparatus, a device management system, and a device management method.

BACKGROUND

There is always a potential risk that a failure caused by a design specification or a manufacturing defect in parts included in a device will occur similarly in other devices including the same parts.

A device only detects a failure prediction for its own device. Although the risk of failure can be grasped for devices detecting a failure prediction, the risk of failure cannot be grasped for devices not detecting the failure prediction. Therefore, it is difficult to grasp similar potential risks among a plurality of devices at an early stage.

BRIEF DESCRIPTION OF THE DRAWINGS

FIG. 4 is a diagram showing an example of a forwarding management table stored in the memory of the server shown in FIG. 1.

FIG. 5 is a diagram showing another example of the forwarding management table stored in the memory of the server shown in FIG. 1.

FIG. 11 is a diagram showing an example of a flow of the collation processing performed by the processing circuitry of the server shown in FIG. 8.

DETAILED DESCRIPTION

In general, according to one embodiment, a device management apparatus includes processing circuitry. The processing circuitry acquires information indicating occurrence of a first failure prediction of a first device. The processing circuitry adjusts detection sensitivity of a second failure prediction of a second device relating to the information based on relevance between the first device and the second device. The second device is different from the first device.

First Embodiment

A first embodiment will be explained with reference to the drawings.

In the first embodiment, based on a medical device issuing a failure prediction, an adjustment of detection sensitivity of the failure prediction is forwarded to a medical device not issuing the failure prediction. For example, the adjustment of detection sensitivity of the failure prediction is an adjustment for the failure prediction to be detected easier. For example, the adjustment for the failure prediction to be detected easier is achieved by increasing the detection sensitivity of the failure prediction. The first embodiment is an example of a medical device issuing a failure prediction and a medical device not issuing the failure prediction existing in the same hospital. A failure prediction is an indicator indicating that, although a failure has not yet occurred in a medical device, there is a high probability that a failure or an abnormality may occur to one of the portions in the medical device in the future. A portion is a part of the medical device, and may be in units of parts configuring the medical device, or may be in units of modules assembling a plurality of parts. Hereinafter, the medical device issuing the failure prediction will also be referred to as a source device. The source device may also be referred to as a first device. A medical device that has not issued the failure prediction and is to be an adjustment target of the detection sensitivity of the failure prediction will be referred to as a destination device. The destination device may also be referred to as a second device.

Figure 1:
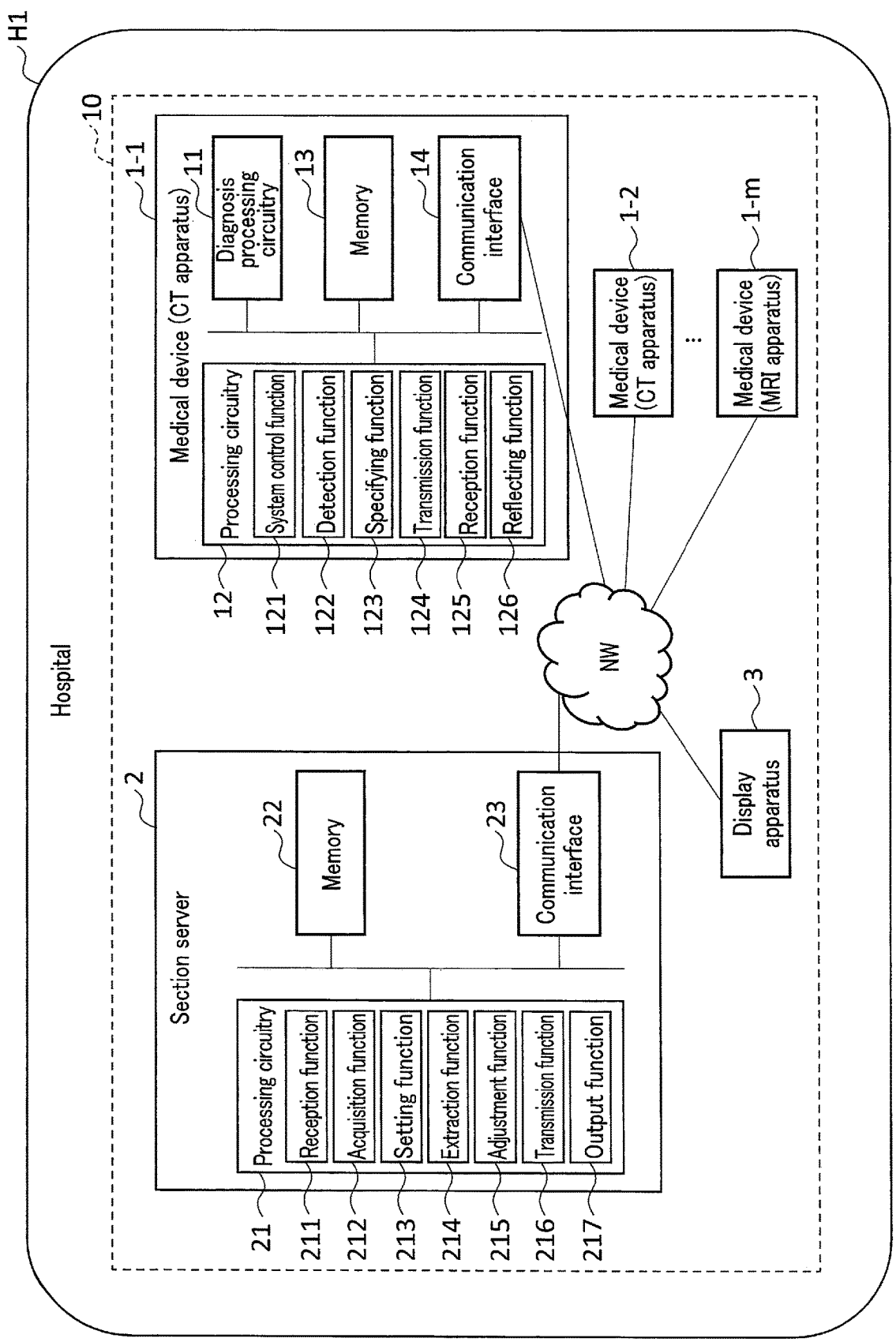
FIG. 1 is a diagram showing a configuration of an in-hospital system according to a first embodiment.

FIG. 1 is a diagram showing a configuration of an in-hospital system 10 according to the first embodiment. As shown in FIG. 1, the in-hospital system 10 is a system configured by a plurality of apparatuses in a hospital H1. The in-hospital system 10 is an example of a device management system.

The in-hospital system 10 includes a plurality of medical devices 1-1 to 1-$m$ ($m$ is an integer equal to or larger than two), a section server 2, and a display apparatus 3. The plurality of medical devices 1-1 to 1-$m$, the section server 2, and the display apparatus 3 are connected to each other via an intra-hospital network such as a local area network (LAN) in a communicatory manner. The network connection may be either wired or wireless.

The medical devices 1-1 to 1-$m$ include medical devices of a variety of uses for acquiring data used for diagnosing a patient. Here, the medical device 1-1 and the medical device 1-2 are assumed to be computed tomography (CT) apparatuses. 1-$m$ is assumed to be a magnetic resonance imaging (MRI) apparatus.

The section server 2 is a server used by a system managing information on test appointments, etc. at a medical care division. For example, the section server 2 is a server used by a radiology information system (RIS) managing information on test appointments, etc. at a radiology division which is one of the divisions of the medical care division. In FIG. 1, an example of a case in which one section server 2 is used is shown. However, the number of servers is not limited thereto. A plurality of section servers 2 may be provided as needed. The section server 2 is an example of a device management apparatus. The device management system is not limited to the section server 2 in the in-hospital system 10. The device management system may include other servers in the in-hospital system 10, a server in a system different from the in-hospital system 10 in the hospital H1, or a server existing outside the hospital H1, etc.

The display apparatus 3 is an apparatus for displaying various kinds of information. For example, the display apparatus 3 includes a liquid crystal display (LCD) and an organic electro-luminescence display (OELD), etc. For example, the display apparatus 3 displays at least one of information of the destination device or the source device. The display apparatus 3 is an example of an output apparatus.

The medical device 1-1 includes at least diagnosis processing circuitry 11, processing circuitry 12, a memory 13, and a communication interface 14.

The diagnosis processing circuitry 11 is circuitry for executing processing relating to a diagnosis in the medical device 1-1. For example, in the CT apparatus, the diagnosis processing circuitry 11 is circuitry for executing processing relating to imaging.

The processing circuitry 12 includes processors such as a central processing unit (CPU) and a graphics processing unit (GPU). By activating a program installed in the memory 13, etc., the processor executes a system control function 121, a detection function 122, a specifying function 123, a transmission function 124, a reception function 125, and a reflecting function 126, etc. Each of the functions 121 to 126 is not limited to the case of being realized by a single processing circuitry. The processing circuitry may be configured by combining a plurality of independent processors, and may realize each of the functions 121 to 126 by having each of the processors execute the program. Each of the functions 121 to 126 will be described later.

The memory 13 is a storage apparatus, such as a read-only memory (ROM), a random access memory (RAM), a hard disk drive (HDD), a solid-state drive (SSD), and an integrated-circuit storage apparatus, which stores various kinds of information. Other than the above storage apparatus, the memory 13 may be a portable storage medium, such as a compact disc (CD), a digital versatile disc (DVD), and a flash memory, or a driving apparatus that reads and writes various kinds of information between semiconductor memory devices, etc.

The memory 13 stores characteristic data of the medical device 1-1. For example, the characteristic data of the medical device 1-1 includes device information, measurement data relating to an operation status, and data specifying a detection algorithm of the failure prediction.

The device information is information specifying the medical device 1-1. The device information may include a list of portions configuring the device, and a type, a model number, and a production lot of the device, etc. For example, the portion may be a monitor. For example, the type of device may be a CT apparatus. For example, the model number may be a number specifying the model of the device. For example, the production lot may be a production number.

The measurement data relating to an operation status is data obtained by measuring the status of operation of the medical device 1-1. The measurement data relating to an operation status includes measurement data relating to an operation and measurement data relating to usage, etc.

The measurement data relating to an operation is data obtained by measuring an event that has occurred corresponding to the operation of the medical device 1-1. For example, the measurement data relating to an operation includes data relating to an operation environment such as vibration data, temperature data, and audio data, and current value data and voltage value data.

The vibration data is data relating to vibration of the medical device 1-1. The vibration data is measured by a sensor (not shown) attached to the medical device 1-1 to supervise its safety. The vibration data may be measured by a sensor attached to a plurality of portions of the medical device 1-1.

The temperature data is data relating to an environmental temperature to which the medical device 1-1 is subjected. The temperature data is measured by a sensor (not shown) attached to the medical device 1-1 to supervise its safety. The temperature data may be measured by a sensor attached to a plurality of portions on the medical device 1-1.

The audio data is data relating to a sound emitted by the medical device 1-1. The audio data may be data relating to a frequency. The data is measured by a sensor (not shown) attached to the medical device 1-1. The audio data may be measured by a sensor attached to a plurality of portions on the medical device 1-1.

The current value data and the voltage value data are data relating a current value and a voltage value at the medical device 1-1. The current value data and the voltage value data are measured by a sensor (not shown) attached to the medical device 1-1. The current value data and the voltage value data may be measured for each portion configuring the medical device 1-1.

The measurement data relating to usage is data obtained by measuring matters that change in accordance with the usage of the measurement data 1-1. The measurement data relating to usage includes data relating to frequency of usage and data relating to used hours, etc. For example, the data relating to frequency of usage includes the number of persons using the medical device 1-1 per day and the number of times of using an application per day. For example, the data relating to used hours includes an average of used hours per day and a total of used hours from installation to the present. The measurement data relating to usage is measured by the processing circuitry 12 in accordance with an on/off of the power of the medical device 1-1 and activation of the application.

The data specifying a detection algorithm is data for specifying a detection algorithm used for detecting a failure prediction and specifying a failure estimation portion. The failure estimation portion is a portion at which a failure has not yet occurred, but is estimated to occur with a high probability in the future. For example, in a case where the detection algorithm includes a later-described failure estimation model generated by machine learning, the data specifying the detection algorithm is version information of the failure estimation model.

The failure estimation model is, for example, a trained model to which the measurement data relating to an operation of the medical device is input, and from which a presence or absence of the failure prediction can be output. The failure estimation model may also be trained to have the measurement data relating to the operation input, and to be able to output the failure estimation portion.

The failure estimation model is generated by the processing circuitry 12 by machine learning using training data in which measurement data relating to the operation of a medical device serves as input data and an occurrence of a failure prediction is used as supervisory data. At least one piece of measurement data among the pieces of measurement data relating to the operation indicates a different trend between a case in which the failure prediction has occurred and a case in which the failure prediction has not occurred. Therefore, there is a certain correlation between the measurement data relating to the operation and the presence or absence of the failure prediction.

Furthermore, the failure estimation model may be generated by machine learning using training data in which the measurement data relating to the operation of the medical device serves as the input data and the failure estimation portion at which the failure prediction has occurred is used as the supervisory data. At least one piece of measurement data among the pieces of measurement data relating to the operation indicates a different trend between a case in which the failure prediction has occurred and a case in which the failure prediction has not occurred. At least one piece of measurement data among the pieces of measurement data relating to the operation indicates a different trend for each failure estimation portion. Therefore, there is a certain correlation between the measurement data relating to the operation and the failure estimation portion.

The failure estimation model may also be designed to be able to output a cause of the occurrence of the failure prediction. For example, when predetermined data is input to the failure estimation model, at least one feature amount that is different from the last output is output from the failure estimation model, and a cause relating to the output feature amount is estimated.

The communication interface 14 is an interface for performing data communications with other computers. For example, the communication interface 14 performs various data communications with the section server 2 via an intra-hospital network in conformity with a known preset standard.

Each of the functions 121 to 126 will be explained.

The system control function 121 controls each unit in the medical device 1-1 based on input information that is input.

The detection function 122 detects a failure prediction of its own medical device 1-1. For example, by the detection algorithm, the detection function 122 detects the presence or absence of the failure prediction of the medical device 1-1 by using, for example, the above-mentioned failure estimation model. The detection function 122 detects the presence or absence of the failure prediction of the medical device 1-1 by executing the detection algorithm at an appropriate timing, such as prior to the opening time of the hospital H1, after the closing time of the hospital H1, and when the operation of the medical device 1-1 is suspended.

By the detection algorithm, the specifying function 123 specifies the failure estimation portion of the medical device 1-1 by using, for example, the above-mentioned failure estimation model. By the detection algorithm, the specifying function 123 may estimate a failure estimation cause of the failure estimation portion using the above-mentioned failure estimation model.

The transmission function 124 transmits maintenance data to the section server 2 via the communication interface 14 based on detection of the failure prediction by the detection function 122. For example, the maintenance data includes a failure prediction analysis result and characteristic data of the medical device 1-1. For example, the failure prediction analysis result includes information indicating occurrence of the failure prediction. In the case where the failure estimation portion is specified by the specifying function 123, the failure prediction analysis result includes information indicating the failure estimation portion. The failure prediction analysis result may also include information indicating a failure estimation cause of the failure estimation portion. For example, the maintenance data is used for extracting a destination device by the section server 2. Furthermore, the transmission function 124 transmits the characteristic data to the section server 2 at, for example, a predetermined cycle via the communication interface 14.

The reception function 125 receives adjustment information of detection sensitivity of the failure prediction (hereinafter, simply referred to as "adjustment information") adjusted by the section server 2 described later via the communication interface 14. The adjustment information includes information indicating adjustment details of the detection algorithm for adjusting the detection sensitivity of the failure prediction and adjustment instructions of the detection algorithm. For example, in a case where the detection algorithm includes the failure estimation model, the adjustment information includes training data for further training the failure estimation model as information indicating the adjustment details of the detection algorithm. Furthermore, for example, the adjustment information may also include information relating to execution frequency.

The reflecting function 126 reflects the adjustment information on a detection algorithm stored in the memory 13. "Reflecting" includes the meaning of updating, applying, adjusting, changing, and relearning, etc., regardless of whether it is temporarily or continuously. In this manner, the detection function 122 and the specifying function 123 use a detection algorithm on which the algorithm for adjusting the detection sensitivity of the failure prediction is reflected. In accordance with the reception of the adjustment information, the reflecting function 126 may automatically reflect the adjustment information on the detection algorithm. Instead of this, the reflecting function 126 may reflect the adjustment information on the detection algorithm based on a direct or a remote input of a reflecting instruction by a manager of the in-hospital system 10.

The medical devices 1-2 to 1-$m$ may be configured in the same manner as the medical device 1-1 described above. Therefore, the explanations thereof will be omitted.

The section server 2 also has a function of forwarding the adjustment of the detection sensitivity of the failure prediction to the destination device based on the source device.

The section server 2 includes at least processing circuitry 21, a memory 22, and a communication interface 23.

In the same manner as the processing circuitry 12, the processing circuitry 21 includes a processor such as a CPU or a GPU. By activating a program installed in the memory 13, etc., the processor executes a reception function 211, an acquisition function 212, a setting function 213, an extraction function 214, an adjustment function 215, a transmission function 216, and an output function 217, etc. Each of the functions 211 to 217 will be described later.

Similar to the memory 13, the memory 22 is a storage apparatus such as a ROM, a RAM, an HDD, an SSD, and an integrated circuit storage apparatus configured to store various kinds of information. For example, the memory 22 stores characteristic data of each of the medical devices 1-1 to 1-$m$. For example, the section server 2 acquires the characteristic data of the medical device at an appropriate timing or on a regular basis from the medical devices 1-1 to 1-$m$, and stores it in the memory 22. The characteristic data of each of the medical devices 1-1 to 1-$m$ is used to extract a destination device.

The memory 22 stores an extraction item management table. The extraction item management table is a look up table (LUT) or a database associating the failure estimation portion with one or more extraction items. The extraction item is an item indicating a condition for extracting the destination device. The extraction item is used to configure the extraction condition for extracting the destination device. The extraction item is an item that can be collated with the characteristic data of each of the medical devices 1-1 to 1-$m$. The extraction condition is a condition for extracting a medical device that corresponds to all of the extraction items configuring the extraction condition as the destination device. The extraction condition is a condition for extracting the destination device. A configuration example of the extraction item management table will be described later.

The memory 22 stores a forwarding management table. In one example, the forwarding management table is an LUT or a database in which the failure estimation portion is associated with the necessity of forwarding. The necessity of forwarding indicates the necessity of adjustment of the detection sensitivity of the failure prediction with respect to the destination device. In another example, the forwarding management table is an LUT or a database in which the failure estimation cause of the failure estimation portion is associated with the necessity of forwarding. A configuration example of the forwarding management table will be described later.

The communication interface 23 is an interface for performing data communications with other computers. For example, the communication interface 23 performs various data communications with each of the medical devices 1-1 to 1-$m$ and the display apparatus 3 via the intra-hospital network in conformity with a known preset standard.

Each of the functions 211 to 217 will be described.

The reception function 211 receives the maintenance data from one of the source devices among the medical devices 1-1 to 1-$m$ via the communication interface 23. For example, the reception function 211 can receive the maintenance data as a response to a request for the maintenance data transmitted from the section server 2 to the medical devices 1-1 to 1-$m$. For example, the reception function 211 can receive the maintenance data autonomously transmitted by the source device. The reception function 211 receives the characteristic data from one of the medical devices 1-1 to 1-$m$ via the communication interface 23. For example, the reception function 211 can receive the characteristic data as a response to a request for the characteristic data transmitted from the section server 2 to the medical devices 1-1 to 1-$m$. For example, the reception function 211 can receive the maintenance data autonomously transmitted by the source device on a regular basis.

The acquisition function 212 includes a function for acquiring information indicating the occurrence of the failure prediction of the source device. For example, the acquisition function 212 acquires information indicating the occurrence of the failure prediction of the source device from the maintenance data received by the reception function 211. Furthermore, the acquisition function 212 includes a function for acquiring information indicating the failure estimation portion of the source device. For example, the acquisition function 212 acquires the information indicating the failure estimation portion of the source device from the maintenance data received by the reception function 211.

The setting function 213 sets the extraction condition. For example, in a case where the acquisition function 212 acquires the information indicating the occurrence of the failure prediction of the source device and does not acquire the information indicating the failure estimation portion of the source device, the setting function 213 sets the device, the model number, or the production lot corresponding to the source device as the extraction condition in accordance with a predetermined rule. For example, in a case where the acquisition function 212 acquires the information indicating the failure estimation portion of the source device, the setting function 213 sets the extraction condition based on the failure estimation portion of the source device acquired by the acquisition function 212. In this example, the setting function 213 uses the extraction item management table to acquire one or more extraction items associated with the failure estimation portion of the source device acquired by the acquisition function 212. The setting function 213 sets a condition corresponding to all of the one or more extraction items as the extraction condition. The extraction condition is an example of relevance between the source device and one or more destination devices.

The extraction function 214 extracts one or more destination devices from among a plurality of medical devices under the extraction condition set by the setting function 213. For example, the extraction function 214 collates the characteristic data of each of the medical devices 1-1 to 1-$m$ stored in the memory 22 with all of the extraction items configuring the extraction condition. The extraction function 214 extracts one or more medical devices that correspond to all of the extraction items configuring the extraction condition as the destination device. The destination device included in the extraction condition may be considered to be a device that is highly relevant and similar to the source device.

The adjustment function 215 adjusts the detection sensitivity of the failure prediction of the destination device relating to at least the information indicating the occurrence of the failure prediction based on the relevance between the source device and one or more destination devices. For example, in a case where the acquisition function 212 acquires the information indicating the occurrence of the failure prediction of the source device and does not acquire the information indicating the failure estimation portion of the source device, the adjustment function 215 adjusts the detection sensitivity of the failure prediction of the source device. For example, in a case where the acquisition function 212 acquires the information indicating the failure estimation portion of the source device, the adjustment function 215 adjusts the detection sensitivity of the failure prediction at a portion corresponding to the failure estimation portion for the destination device. An example of adjusting the detection sensitivity of the failure prediction will be described later.

The transmission function 216 transmits the adjustment information based on the adjustment by the adjustment function 215 to the destination device via the communication interface 23.

The output function 217 outputs at least one of the information of the source device or the information of the destination device to the display apparatus 3. For example, the information of the source device includes information specifying the source device. The information of the source device may also include information relating to the failure prediction. The information relating to the failure prediction includes the information indicating the occurrence of the failure prediction. The information relating to the failure prediction may also include information specifying the failure estimation portion. The information of the source device is based on the maintenance data. The information specifying the source device is information indicating a CT apparatus, etc. The information specifying the failure estimation portion is information indicating an X-ray tube, etc. The information of the destination device includes information specifying the destination device and the adjustment information of the detection sensitivity. The information of the destination device is based on the extraction of the destination device by the extraction function 214. The adjustment information of the detection sensitivity is based on the adjustment of the detection sensitivity by the adjustment function 215.

The output function 217 may output at least the information relating to the prediction of a failure that occurred with respect to the source device to the display apparatus 3.

The extraction condition will be explained.

Figures 2, 3:
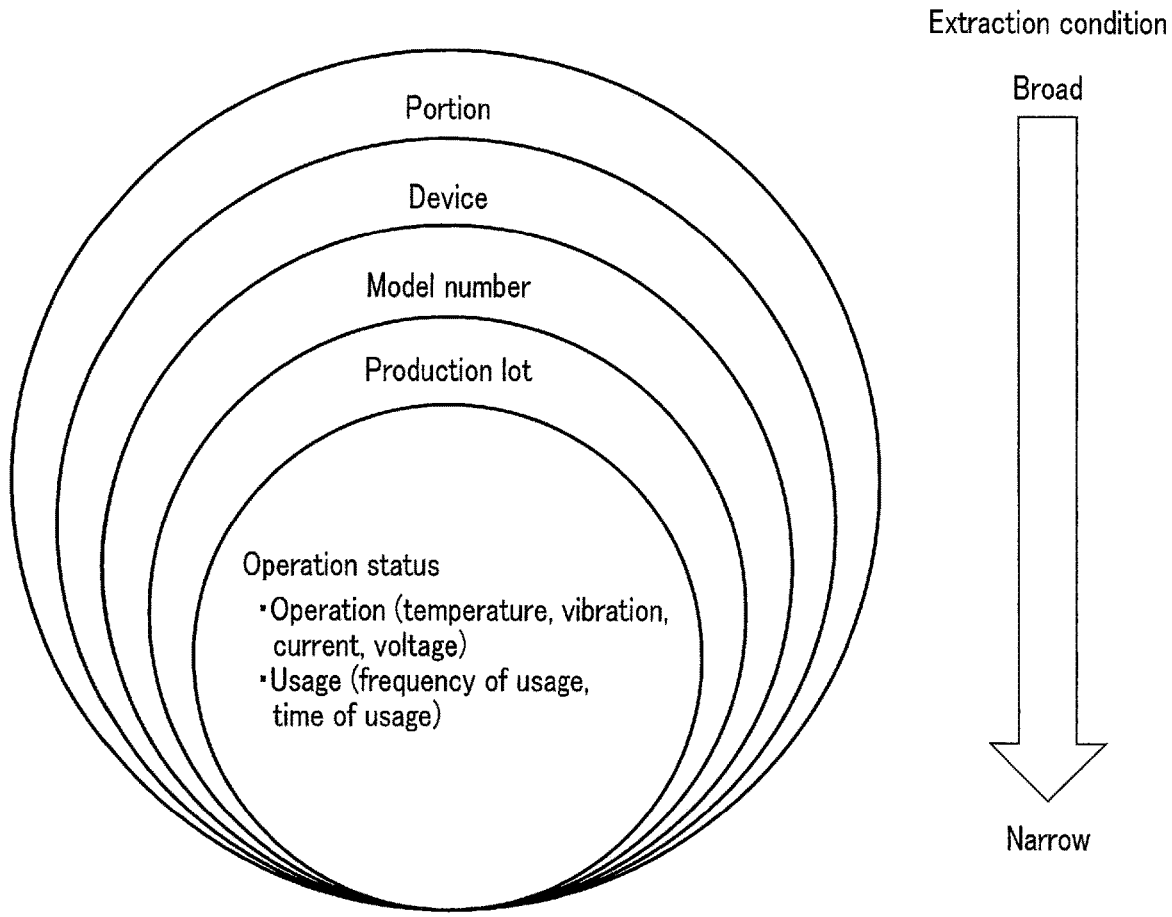
FIG. 2 is a diagram showing an example of a range of extraction conditions.
FIG. 3 is a diagram showing an example of an extraction item management table stored in a memory of a server shown in FIG. 1.

FIG. 2 is a diagram showing an example of a range of the extraction condition. The range of the extraction condition corresponds to the number of medical devices included in the extraction condition. For example, extraction items include a portion, a device, a model number, a production lot, and an operation status.

In a case where the portion is the extraction item, the extraction item is an item indicating extraction of a device including the same portion as that of the source device. In a case where the device is the extraction item, the extraction item is an item indicating extraction of a device that is the same as the source device. The extraction condition under which the device is the extraction item is narrower than the extraction condition under which the portion is the extraction item, and is included in the extraction condition under which the portion is the extraction item. In a case where the model number is the extraction item, the extraction item is an item indicating extraction of a device with the same model number as that of the source device. The extraction condition under which the model number is the extraction item is narrower than the extraction condition under which the device is the extraction item, and is included in the extraction condition under which the device is the extraction item. In a case where the production lot is the extraction item, the extraction item is an item indicating extraction of a device with the same production lot as that of the source device. The extraction condition under which the production lot is the extraction item is narrower than the extraction condition under which the model number is the extraction item, and is included in the extraction condition under which the model number is the extraction item.

In a case where the operation status is the extraction item, the extraction item is an item indicating extraction of the same operation status as that of the source device. For example, the operation status indicates a status of a device that is subjected to an environmental temperature equal to or more than 30 degrees Celsius, a device that is used by X or more users per day, and a device on which an application is used Y or more times per day. The operation status does not indicate the characteristic of the device itself. Therefore, the extraction condition under which the operation status is the extraction item may be narrower or wider than the extraction condition under which the production lot, the model number, or the device is the extraction item.

A configuration example of the extraction item management table will be explained.

FIG. 3 is a diagram showing an example of the extraction item management table stored in the memory 22 of the section server 2.

The extraction item management table associates the failure estimation portion with one or more extraction items. The "failure estimation portion" of the extraction item management table comprehensively indicates various kinds of failure estimation portions. The "extraction item" of the extraction item management table indicates one or more extraction items for configuring the extraction condition.

The "extraction item" includes one of the portion, the device, the model number, or the production lot for each of the failure estimation portions. The "extraction item" includes one of the portion, the device, the model number, or the production lot for each of the failure estimation portions to extract a device that is highly relevant and similar to the source device as the destination device. The extraction condition under which the portion is the extraction item is a condition for extracting a medical device including a portion that corresponds to the failure estimation portion. Since the extraction condition under which the device is the extraction item is included in the extraction condition under which the portion is the extraction item, it is a condition for extracting all of or a part of the medical device including a portion that corresponds to the failure estimation portion. Since the extraction condition under which the model number is the extraction item is included in the extraction condition under which the portion is the extraction item, it is a condition for extracting all of or a part of the medical device including a portion that corresponds to the failure estimation portion. Since the extraction condition under which the production lot is the extraction item is included in the extraction condition under which the portion is the extraction item, it is a condition for extracting all of or a part of the medical device including a portion that corresponds to the failure estimation portion. Therefore, the extraction condition that is associated with the failure estimation portion is a condition for extracting a medical device including a portion that corresponds to at least the failure estimation portion as the destination device.

The "extraction item" may include one or more operation statuses in addition to one of the portion, the device, the model number, or the production lot. In a case where the "extraction item" includes one or more operation statuses that may have an effect on the failure of the failure estimation portion, the extraction condition is a condition obtained by considering also the operation status of the source device. That is, the extraction condition is a condition for extracting a device that includes a portion corresponding to the failure estimation portion and corresponds to the operation status of the source device. A device corresponding to the operation status of the source device is a device in which the trend of the operation status is similar to that of the source device. The range of similarity may be set as appropriate. The extraction condition is a condition for extracting a device by narrowing it down to a device highly relevant and similar to the source device.

In the example shown in FIG. 3, the "extraction item" associated with an X-ray tube is a tube current, a filament current, and a gantry temperature. The tube current, the filament current, and the gantry temperature may have an effect on the failure of the X-ray tube. The extraction condition is a condition for extracting a device of the same production lot as the source device, and a device corresponding to the tube current, the filament current, and the gantry temperature of the source device.

One or more extraction items included in the "extraction item" may be set as appropriate. Which of the items of the portion, the device, the model number, or the production lot to include in the "extraction item" may differ depending on the type of the failure estimation portion. Whether or not to include one or more operation statuses in the "extraction item" may differ depending on the type of the failure estimation portion. For example, for a failure estimation portion which is subjected to degradation over time, one or more operation statuses may be included in the "extraction item". The contents of one or more operation statuses included in the "extraction item" may differ depending on the type of the failure estimation portion. Therefore, the extraction condition differs in accordance with the type of the failure estimation portion.

A configuration example of the forwarding management table will be explained.

FIG. 4 is a diagram showing an example of the forwarding management table stored in the memory 22 of the section server 2.

The forwarding management table associates the failure estimation portion with the necessity of forwarding.

The "failure estimation portion" of the forwarding management table comprehensively indicates various kinds of failure estimation portions. For example, in the case where the "failure estimation portion" is portion B, the "necessity of forwarding" in the forwarding management table is "necessary". When "necessity of forwarding" is "necessary", it indicates that it is necessary to adjust the detection sensitivity of the failure prediction at the destination device. In the case where "necessity of forwarding" is "necessary", the processing circuitry 21 determines that it is necessary to adjust the detection sensitivity of the failure prediction at the destination device. On the other hand, when "necessity of forwarding" is "unnecessary", it indicates that it is not necessary to adjust the detection sensitivity of the failure prediction at the destination device. In the case where "necessity of forwarding" is "unnecessary", the processing circuitry 21 determines that it is unnecessary to adjust the detection sensitivity of the failure prediction at the destination device.

The reason for changing the necessity of adjusting the detection sensitivity of the failure prediction at the destination device in accordance with the type of failure estimation portion is as follows. The adjustment of the detection sensitivity of the failure prediction results in increasing the processing load of the destination device. By narrowing down the adjustment of the detection sensitivity of the failure prediction to a case in which the detection probability of the failure prediction is to be increased, the processing circuitry 21 prevents the processing load of the destination device from increasing unnecessarily.

Whether or not the "necessity of forwarding" is "necessary" or "unnecessary" depends on whether the importance of the portion is high or low. The importance is determined depending on the extent to which the detection probability of the failure prediction is to be increased. For example, the importance is determined based on the length of time for the destination device to recover from the failure caused by the failed portion. In a case where the length of time from the failure to the recovery of the destination device is equal to or longer than a certain time, the importance of the portion is high. For the portion with high importance, it is preferable to have the failure prediction detected reliably at the destination device. On the other hand, in a case where the length of time from the failure to the recovery of the destination device is shorter than a certain time, the importance of the portion is low. For the portion with low importance, even if the failure prediction is not detected reliably at the destination device, there is less effect.

For example, a hospital may not have a spare for an expensive portion such as an X-ray tube. In a case where the failed portion is an expensive portion, the time for the destination device to recover from the failure caused by such a portion would be long. Therefore, the importance of an expensive portion is high. For example, in a case where the failed portion can only be replaced by a certain person, the time for the destination device to recover from the failure caused by such a portion would be long. Therefore, the importance is high for a portion that can only be replace by a certain person. For example, when a certain portion fails, other portions may also fail in a linked manner. In a case where the failed portion is a portion that has an effect on other portions in a linked manner, the time for the destination device to recover from the failure caused by such a portion would be long. Therefore, the importance is high for a portion that has an effect on other portions in a linked manner. On the other hand, for example, the importance is low for a portion that is sufficiently stocked at a hospital, and that can be easily replaced by anyone. For example, the importance is low for a portion that has less effect on the performance of the device, when it fails.

Whether or not the "necessity of forwarding" is "necessary" or "unnecessary" may be set in advance, or may be changed as appropriate. For example, the setting of "necessary" or "unnecessary" for the "necessity of forwarding" may be changed for each hospital. For a hospital on, such as, an isolated island, time is required to supply parts. Therefore, the "necessity of forwarding" may mostly be set to "necessary".

It should be noted that the forwarding management table may associate the failure estimation portion with points instead of the necessity of forwarding. In this example, the points are allocated for each portion in accordance with the importance of the portion. In this example, in a case where the points are equal to or higher than a threshold value, the processing circuitry 21 determines that it is necessary to adjust the detection sensitivity of the failure prediction at the destination device. On the other hand, in a case where the points are lower than the threshold value, the processing circuitry 21 determines that it is unnecessary to adjust the detection sensitivity of the failure prediction at the destination device. The threshold value may be set in advance, or may be changed as appropriate. The threshold value may be changed for each hospital.

FIG. 5 is a diagram showing another example of the forwarding management table stored in the memory 22 of the section server 2. FIG. 5 shows an example of the forwarding management table in which an ultrasound probe is the failure estimation portion. The memory 22 stores the forwarding management table for each failure estimation portion.

The forwarding management table associates a failure estimation cause of the failure estimation portion with the necessity of forwarding.

The "estimation cause of failure estimation portion" of the forwarding management table comprehensively indicates various kinds of failure estimation causes. For example, in a case where the "estimation cause of failure estimation portion" is a heated ultrasound probe, the "necessity of forwarding" in the forwarding management table is "necessary". When the "necessity of forwarding" is "necessary", it indicates that it is necessary to adjust the detection sensitivity of the failure prediction at the destination device. On the other hand, when the "necessity of forwarding" is "unnecessary", it indicates that it is not necessary to adjust the detection sensitivity of the failure prediction at the destination device. The reason for changing the necessity of adjusting the detection sensitivity of the failure prediction at the destination device in accordance with the failure estimation cause is as follows. The adjustment of the detection sensitivity of the failure prediction results in increasing the processing load of the destination device. By narrowing down the adjustment of the detection sensitivity of the failure prediction to a case in which the detection probability of the failure prediction is to be increased, the processing circuitry 21 prevents the processing load of the destination device from increasing unnecessarily.

It is determined whether the "necessity of forwarding" is "necessary" or "unnecessary" depending on whether the degree of risk of the failure estimation cause is high or low. The degree of risk is determined depending on the extent to which the probability of detecting the failure prediction is to be increased. For example, the degree of risk is determined based on the probability of erroneous diagnosis caused by the failed portion to occur or the probability of patient injury caused by the failed portion to occur. In the case where the probability of erroneous diagnosis caused by the failed portion to occur or the probability of patient injury caused by the failed portion to occur is high, the degree of risk of the failure estimation cause is high. For a portion with a high degree of risk, it is preferable to have the failure prediction detected reliably at the destination device. On the other hand, in the case where the probability of erroneous diagnosis caused by the failed portion or the probability of patient injury caused by the failed portion is low, the degree of risk is low. For a portion with a low degree of risk, even if the failure prediction is not detected reliably at the destination device, there is less effect.

For example, there is a possibility that a heated ultrasound probe may burn a patient. Therefore, the degree of risk of the heated ultrasound probe is high. For example, there is a high probability that a defective element of the ultrasound probe may cause erroneous diagnosis. Therefore, the degree of risk of the defective element of an ultrasound probe is high. For example, for a cable breakage of the ultrasound probe, there is a high probability that a manager himself/herself of the in-hospital system 10 may notice a malfunction. Therefore, the degree of risk of the cable breakage of the ultrasound probe is low.

The setting of whether the "necessity of forwarding" is "necessary" or "unnecessary" may be determined in advance, or may be changed as appropriate. For example, the setting of "necessary" or "unnecessary" for the "necessity of forwarding" may be changed for each hospital.

It should be noted that the forwarding management table may associate the failure estimation cause with points instead of associating the failure estimation portion with the necessity of forwarding. In this example, the points are allocated for each estimation cause in accordance with the degree of risk of the failure estimation cause. In this example, in a case where the points are equal to or higher than a threshold value, the processing circuitry 21 determines that it is necessary to adjust the detection sensitivity of the failure prediction at the destination device. On the other hand, in a case where the points are lower than the threshold value, the processing circuitry 21 determines that it is unnecessary to adjust the detection sensitivity of the failure prediction at the destination device. The threshold value may be determined in advance, or may be changed as appropriate. The threshold value may be changed for each hospital.

Hereinafter, processing of the section server 2 will be explained in detail.

Figure 6:
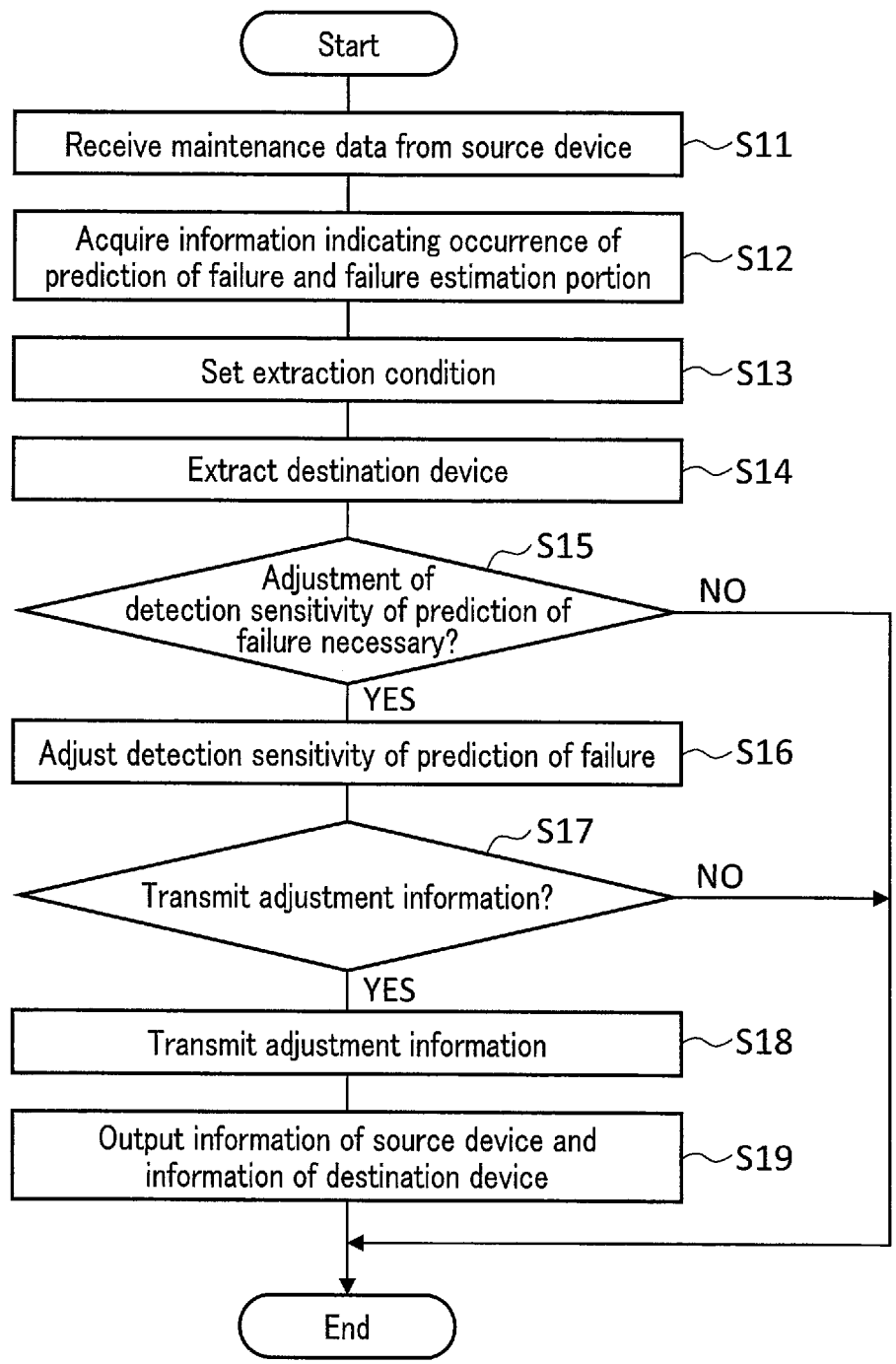
FIG. 6 is a diagram showing an example of a flow of forwarding processing performed by processing circuitry of the server shown in FIG. 1.

FIG. 6 is a diagram showing an example of a flow of forwarding processing performed by the processing circuitry 21 of the section server 2. The order of processing may be changed, and a part of the processing may be omitted, as appropriate.

Here, the medical device 1-1 is assumed to be the source device. The medical device 1-2 is assumed to be the destination device.

By the reception function 211, the processing circuitry 21 receives maintenance data from the medical device 1-1, which is the source device, via the communication interface 23 (step S11).

By the acquisition function 212, the processing circuitry 21 acquires, for example, information indicating occurrence of the failure prediction of the medical device 1-1 from the maintenance data (step S12). Furthermore, in step S12, by the acquisition function 212, the processing circuitry 21 acquires, for example, information indicating a failure estimation portion of the medical device 1-1.

By the setting function 213, the processing circuitry 21 sets an extraction condition (step S13). In step S13, for example, in a case where the processing circuitry 21 acquires the information indicating the occurrence of the failure prediction of the source device and does not acquire the information indicating the failure estimation portion of the source device, the processing circuitry 21 sets the device, the model number, or the production lot corresponding to the source device as the extraction condition in accordance with a predetermined rule. Furthermore, for example, in a case where the processing circuitry 21 acquires the information indicating the failure estimation portion of the source device, the processing circuitry 21 sets the extraction condition based on the failure estimation portion with reference to the above-mentioned extraction item management table.

In step S13, for example, the processing circuitry 21 may refer to the above-mentioned extraction item management table and set a different extraction condition for each of the acquired failure estimation portions. For example, the processing circuitry 21 changes the range of the extraction condition. In this manner, the processing circuitry 21 is able to set a suitable extraction condition in accordance with the type of failure estimation portion. As a result, the processing circuitry 21 is able to prevent the processing load of the destination device from increasing unnecessarily.

In step S13, for example, the processing circuitry 21 may refer to the above-mentioned extraction item management table and set an extraction condition in consideration of the operation status of the source device. That is, the processing circuitry 21 sets the extraction condition to a condition for extracting a device that includes a portion corresponding to the failure estimation portion and corresponds to the operation status of the source device. In this manner, the processing circuitry 21 is able to set an extraction condition for extracting a device by narrowing it down to a device highly relevant and similar to the source device. As a result, the processing circuitry 21 is able to prevent the processing load of the destination device from increasing unnecessarily.

By the extraction function 214, the processing circuitry 21 extracts, for example, the medical device 1-2 as the destination device from among the medical devices 1-1 to 1-$m$ included in the in-hospital system 10 under the extraction condition (step S14). The destination device extracted in step S14 is a device relating to information indicating at least the occurrence of failure prediction extracted based on the extraction condition.

By the adjustment function 215, the processing circuitry 21 determines whether or not to adjust the detection sensitivity of the failure prediction of the medical device 1-2 (step S15). In step S15, the processing circuitry 21 may refer to the above-mentioned forwarding management table and determine the necessity of adjusting the detection sensitivity of the failure prediction of the medical device 1-2.

In step S15, in one example, the processing circuitry 21 refers to the above-mentioned forwarding management table and determines the necessity of adjusting the detection sensitivity of the failure prediction for each of the failure estimation portions. In this manner, the processing circuitry 21 is able to adjust the detection sensitivity of the failure prediction by narrowing the target down to the failure estimation portion for which the probability of detecting the failure prediction is to be increased. As a result, the processing circuitry 21 is able to prevent the processing load of the destination device from increasing unnecessarily.

In step S15, in another example, the processing circuitry 21 refers to the above-mentioned forwarding management table and determines the necessity of adjusting the detection sensitivity of the failure prediction based on the estimation cause of the failure estimation portion. In this manner, the processing circuitry 21 is able to adjust the detection sensitivity of the failure prediction by narrowing down the target to the estimation cause for which the probability of detecting the failure prediction is to be increased. As a result, the processing circuitry 21 is able to prevent the processing load of the destination device from increasing unnecessarily.

In the case where the processing circuitry 21 determines that it is unnecessary to adjust the detection sensitivity of the failure prediction (step S15, NO), the forwarding processing ends without adjusting the detection sensitivity of the failure prediction at the medical device 1-2.

In the case where the processing circuitry 21 determines that it is necessary to adjust the detection sensitivity of the failure prediction (step S15, YES), the detection sensitivity of the failure prediction is adjusted at the medical device 1-2 (step S16). In step S16, for example, in a case where the processing circuitry 21 acquires the information indicating the occurrence of the failure prediction of the source device and does not acquire the information indicating the failure estimation portion of the source device, the detection sensitivity of the failure prediction of the destination device is adjusted. For example, in a case where the processing circuitry 21 acquires the information indicating the failure estimation portion of the source device, the detection sensitivity of the failure prediction at a portion corresponding to the failure estimation portion is adjusted for the destination device.

In step S16, the adjustment function 215 is able to adjust the detection sensitivity of the failure prediction in the manner exemplified below.

The adjustment function 215 is able to improve the quality of supervisory data of the failure estimation model. The adjustment function 215 may apply data for specifying the failure estimation portion at the source device to the destination device as the training data. For example, the data for specifying the failure estimation portion at the source device includes data obtained by associating measurement data relating to the operation of the source device contributing to the specification of the failure estimation portion with whether or not the failure estimation portion is specified.

The reason for applying the data for specifying the failure estimation portion at the source device to the destination device as the training data is as follows. A plurality of medical devices use the same failure estimation model upon shipping. The medical devices each add data acquired at its own device thereto as supervisory data, and update the failure estimation model by machine learning. The failure estimation model used at a certain device may become a model different from the failure estimation model used at other devices with the passage of time. Therefore, even if the devices start being used at around the same time, some devices may and some devices may not be able to detect the failure prediction. The destination device is able to use data for specifying the failure estimation portion at the source device as the training data and update the failure estimation model. As a result, the destination device is able to increase the probability of detecting the failure prediction of portion corresponding to the failure estimation portion.

By the transmission function 216, the processing circuitry 21 determines whether or not to transmit adjustment information based on the adjustment by the adjustment function 215 to the medical device 1-2 (step S17). In step S17, the processing circuitry 21 may determine the necessity of transmitting the adjustment information in accordance with whether or not a transmission instruction is input by the manager of the in-hospital system 10. In the case where the processing circuitry 21 determines that it is unnecessary to transmit the adjustment information (step S17, NO), the forwarding processing ends without transmitting the adjustment information to the medical device 1-2. In the case where the processing circuitry 21 determines that it is necessary to transmit the adjustment information (step S17, YES), the adjustment information is transmitted to the medical device 1-2 via the communication interface 23 (step S18).

By the output function 217, the processing circuitry 21 outputs at least one of the information of the medical device 1-1 or the information of the medical device 1-2 to the display apparatus 3 (step S19). In this manner, the display apparatus 3 displays at least one of the information of the medical device 1-1 or the information of the medical device 1-2. In step S19, by the output function 217, the processing circuitry 21 may output at least the information relating to the prediction of a failure that occurred with respect to the medical device 1-1 to the display apparatus 3. In this manner, the display apparatus 3 displays at least the information relating to the prediction of a failure that occurred with respect to the medical device 1-1.

It should be noted that, in step S19, the processing circuitry 21 may output the information to an output apparatus other than the display apparatus 3. For example, the output apparatus may be a printer. In this manner, the manager of the in-hospital system 10 is able to confirm at least one of the information of the medical device 1-1 or the information of the medical device 1-2. Alternatively, the manager of the in-hospital system 10 is able to confirm at least the information relating to the prediction of a failure that occurred with respect to the medical device 1-1.

According to the first embodiment, by adjusting the detection sensitivity of the failure prediction at the destination device, the section server 2 is able to grasp a potential failure prediction risk at the destination device at an early stage.

Various modified examples will be explained below.

In the above, an example of each of the medical devices 1-1 to 1-*m* detecting the failure prediction at its own device and specifying the failure estimation portion was explained. However, it is not limited thereto. The section server 2 may detect the failure prediction of each of the medical devices 1-1 to 1-*m* and specify the failure estimation portion.

In this example, the section server 2 includes the detection function 122, the specifying function 123, and the reflecting function 126. The section server 2 stores the detection algorithm of each of the medical devices 1-1 to 1-*m* in the memory 22. The section server 2 intermittently acquires the measurement data relating to the operation from each of the medical devices 1-1 to 1-*m*. The detection function 122 detects the failure prediction of each of the medical devices by the measurement data relating to the operation and the detection algorithm. The specifying function 123 specifies the failure estimation portion by the measurement data relating to the operation and the detection algorithm. The reflecting function 126 reflects the adjustment information on the detection algorithm stored in the memory 22.

In the above, an example of the source device and the destination device being medical devices managed by the section server 2 was explained. However, it is not limited thereto. The source device and the destination device may also be medical devices that are respectively managed by different section servers. In this example, a server (not shown) connected to each section server is prepared, and each of the functions 211 to 217 is implemented on this server.

In the above, an example of the source device and the destination device being medical devices was explained. However, it is not limited thereto. The source device and the destination device may also be various kinds of devices, such as servers. The "device" is assumed to include facilities.

In the above, the failure estimation model was used to explain an example of the detection algorithm. However, it is not limited thereto. The detection algorithm may be analysis processing of measurement data relating to an operation. In this example, the detection algorithm may include a threshold value or a reference that is used for detecting the failure prediction, specifying the failure estimation portion, and specifying the failure estimation cause. The detection algorithm may include a sampling interval of the measurement data relating to the operation. The detection algorithm may include frequency of detecting the failure prediction, specifying the failure estimation portion, and specifying the failure estimation cause. The detection algorithm may include a quality of the measurement data relating to the operation used for detecting the failure prediction, specifying the failure estimation portion, and specifying the failure estimation cause. For example, the quality of the measurement data is filtered data or non-filtered raw data.

The adjustment function 215 may alleviate the threshold value or the reference. The adjustment function 215 may alleviate the threshold value or the reference by narrowing down the target to the measurement data relating to an operation relating to a portion corresponding to the failure estimation portion. In this example, the adjustment information includes a threshold value or a reference which is alleviated as information indicating the adjustment content of the detection algorithm, and includes an update instruction of the threshold value or the reference as an adjustment instruction of the detection algorithm. The adjustment function 215 may shorten the sampling interval of the measurement data relating to the operation. In this example, the adjustment information includes a shortened sampling interval as information indicating the adjustment content of the detection algorithm, and includes an update instruction of the sampling interval as an adjustment instruction of the detection algorithm. The adjustment function 215 may increase the frequency of detecting the failure prediction, specifying the failure estimation portion, and specifying the failure estimation cause. In this example, the adjustment information includes the increased frequency as information indicating the adjustment content of the detection algorithm, and includes an update instruction of the frequency as an adjustment instruction of the detection algorithm. The adjustment function 215 may improve the quality of data so that the raw data of the measurement data relating to the operation may be used for detecting the failure prediction, specifying the failure estimation portion, and specifying the failure estimation cause. The adjustment function 215 may improve the quality by narrowing down the target to the measurement data relating to an operation relating to a portion corresponding to the failure estimation portion. In this example, the adjustment information includes types of data to be used as information indicating the adjustment content of the detection algorithm, and includes an update instruction of the data quality as an adjustment instruction of the detection algorithm. It should be noted that the adjustment function 215 may also narrow down the granularity of the target for adjusting the detection sensitivity of the failure prediction to per part, and not per module. In this manner, the destination device is able to detect the failure prediction in a more precise unit.

Second Embodiment

Hereinafter, a second embodiment will be explained with reference to the drawings.

In the same manner as the first embodiment, the second embodiment forwards an adjustment of a detection sensitivity of a failure prediction to a destination device based on a source device. The second embodiment is different from the first embodiment in that it is an example of the source device and the destination device being in different hospitals.

For configurations that are the same as those of the first embodiment, the same symbols will be used, and the explanations thereof will be omitted. In the second embodiment, portions different from those of the first embodiment will be mainly explained.

Figure 7:
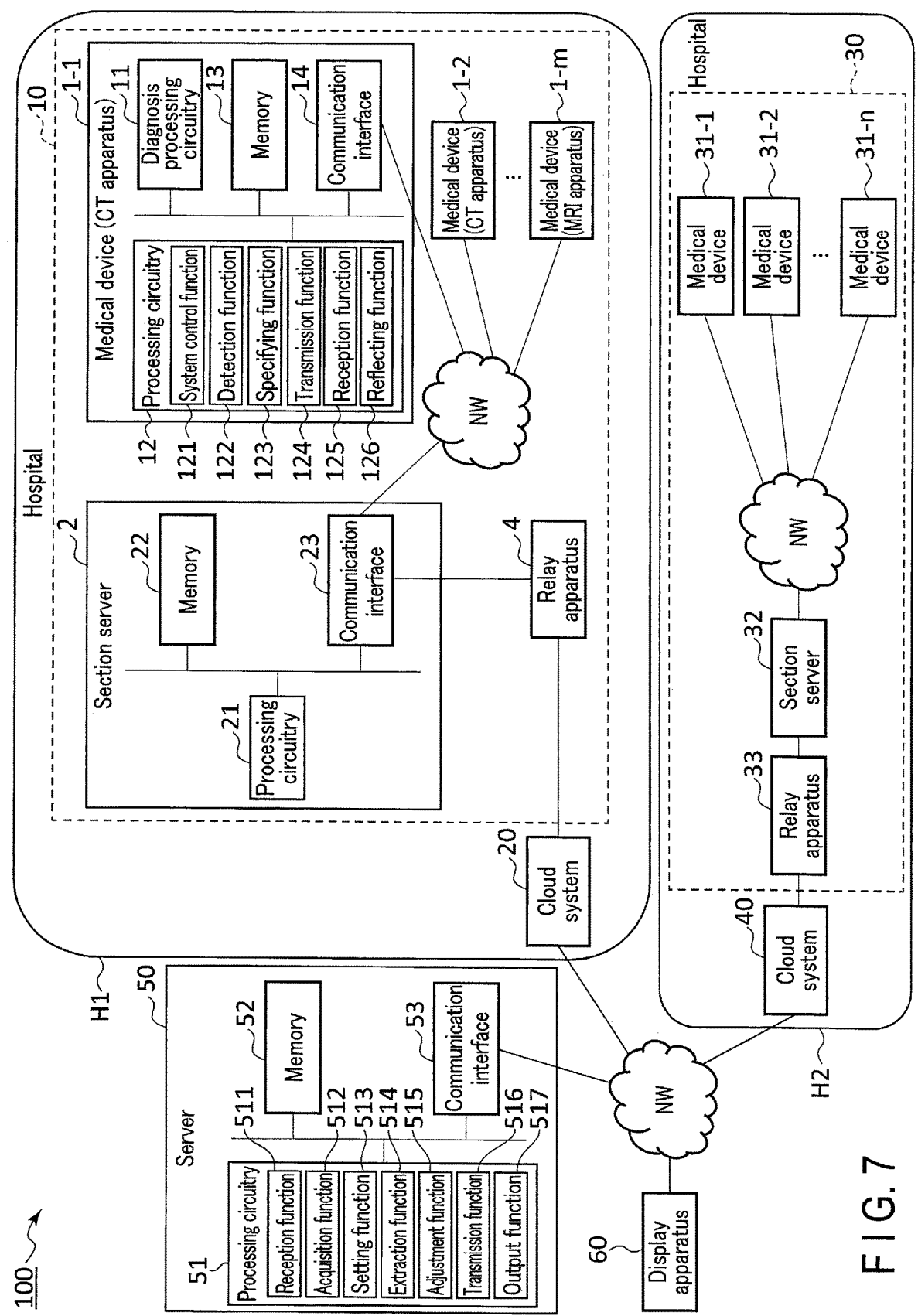
FIG. 7 is a diagram showing a configuration of an information management system according to a second embodiment.

FIG. 7 is a diagram showing a configuration of an information management system 100 according to a second embodiment.

The information management system 100 includes an in-hospital system 10 in a hospital H1, a cloud system 20 in the hospital H1, an in-hospital system 30 in a hospital H2, a cloud system 40 in the hospital H2, a server 50, and a display apparatus 60. The in-hospital system 10 and the cloud system 20 are connected by, for example, a dedicated line. The in-hospital system 30 and the cloud system 40 are connected by, for example, a dedicated line. The server 50 is connected to the cloud system 20 and the cloud system 40 via a network in a manner that enables data communications. The network may be either wired or wireless.

The information management system 100 is a network system that complies with guidelines used when storing medical information in a public cloud, etc., such as three guidelines issued by the three ministers of the Ministry of Health, Labour and Welfare, the Ministry of Economy, Trade and Industry, and the Ministry of Public Management, Home Affairs, Posts and Telecommunications, i.e., three guidelines of three ministries. That is, the information management system 100 is a network system that complies with "Guidelines for safety management of medical information systems" specified by the Ministry of Health, Labour and Welfare, "Safety management guide for information processing companies that manage medical information on a contract basis" specified by the Ministry of Economy, Trade and Industry, and "Guidelines for safety management when cloud service providers handle medical information" specified by the Ministry of Public Management, Home Affairs, Posts and Telecommunications.

The in-hospital system 10 includes a relay apparatus 4 in addition to the plurality of medical devices 1-1 to 1-*m* and the section server 2 mentioned above. It should be noted that the section server 2 omits executing each of the functions 211 to 217 explained in the first embodiment.

The relay apparatus 4 is connected to the cloud system 20 by a dedicated line, and is connected to the section server 2 via a network in a manner that enables data communications. The relay apparatus 4 receives various types of data from the section server 2. For example, the relay apparatus 4 receives various types of data the section server 2 has acquired from the medical devices 1-1 to 1-*m*. The relay apparatus 4 transmits the various types of data received from the section server 2 to the cloud system 20 via the dedicated line.

The cloud system 20 receives the various types of data from the in-hospital system 10, converts the data into a common standardized form set in advance, accumulates it, and transmits it to the server 50. The cloud system 20 is, for example, a cloud computing system that shares a predetermined function among a plurality of apparatuses via a network and realizes the function in cooperation therewith.

The in-hospital system 30 includes a plurality of medical devices 31-1 to 31-*n* (n is an integer equal to or larger than two), a section server 32, and a relay apparatus 33. The plurality of medical devices 31-1 to 31-*n* and the section server 32 are connected to each other via an intra-hospital network in a communicatory manner. The medical devices 31-1 to 31-*n* may be configured in the same manner as the medical device 1-1 described above. Therefore, the explanations thereof will be omitted. The section server 32 may be configured in the same manner as the section server 2 described above. Therefore, the explanations thereof will be omitted.

The relay apparatus 33 is connected to the cloud system 40 by a dedicated line, and is connected to the section server 32 via a network in a manner that enables data communications. The relay apparatus 33 receives various types of data from the section server 32. For example, the relay apparatus 33 receives various types of data the section server 32 has acquired from the medical devices 31-1 to 31-*n*. The relay apparatus 33 transmits the various types of data received from the section server 32 to the cloud system 40 via the dedicated line.

The cloud system 40 receives the various types of data from the in-hospital system 30, converts the data into a common standardized form set in advance, accumulates it, and transmits it to the server 50. The cloud system 40 is, for example, a cloud computing system that shares a predetermined function among a plurality of apparatuses via a network and realizes the function in cooperation therewith.

The server 50 includes processing circuitry 51, a memory 52, and a communication interface 53. The server 50 is an example of a device management apparatus.

In the same manner as the processing circuitry 12, the processing circuitry 51 includes a processor such as a CPU or a GPU. By activating a program installed in the memory 52, etc., the processor executes a reception function 511, an acquisition function 512, a setting function 513, an extraction function 514, an adjustment function 515, a transmission function 516, and an output function 517, etc. Each of the functions 511 to 517 will be described later.

Similar to the memory 13, the memory 52 is a storage apparatus such as a ROM, a RAM, an HDD, an SSD, and an integrated circuit storage apparatus configured to store various kinds of information. For example, the memory 52 stores various types of data transmitted from the in-hospital system 10 via the cloud system 20. The memory 52 stores various types of data transmitted from the in-hospital system 30 via the cloud system 40.

The communication interface 53 is an interface for performing data communications with other computers. For example, the communication interface 53 performs various data communications with the cloud system 20 and the cloud system 40 via the network in conformity with a known preset standard.

Each of the functions 511 to 517 will be explained.

Each of the functions 511 to 517 are the same as each of the functions 211 to 217 explained in the first embodiment. It should be noted that the extraction function 514 is able to extract a destination device belonging to a different hospital from a hospital to which a source device belongs. The output function 517 is able to output at least one of information of the source device or information of the destination device to the display apparatus 60. Alternatively, the output function 517 is able to output at least information relating to the prediction of a failure that occurred with respect to the source device to the display apparatus 60. The display apparatus 60 is the same as the display apparatus 3. The display apparatus 60 is an example of an output apparatus. The information management system 100 including the server 50 and the display apparatus 60 is an example of a device management system.

According to the second embodiment, the server 50 is able to adjust the detection sensitivity of the failure prediction with respect to a destination device belonging to a different hospital from a hospital to which the source device belongs.

Third Embodiment

Hereinafter, a third embodiment will be explained with reference to the drawings.

The third embodiment collates measurement data relating to an operation of a source device with measurement data relating to an operation of a destination device. The third embodiment is an example of the source device and the destination device being in the same hospital.

For configurations that are the same as those of the first embodiment, the same symbols will be used, and the explanations thereof will be omitted. In the third embodiment, portions different from those of the first embodiment will be mainly explained.

Figure 8:
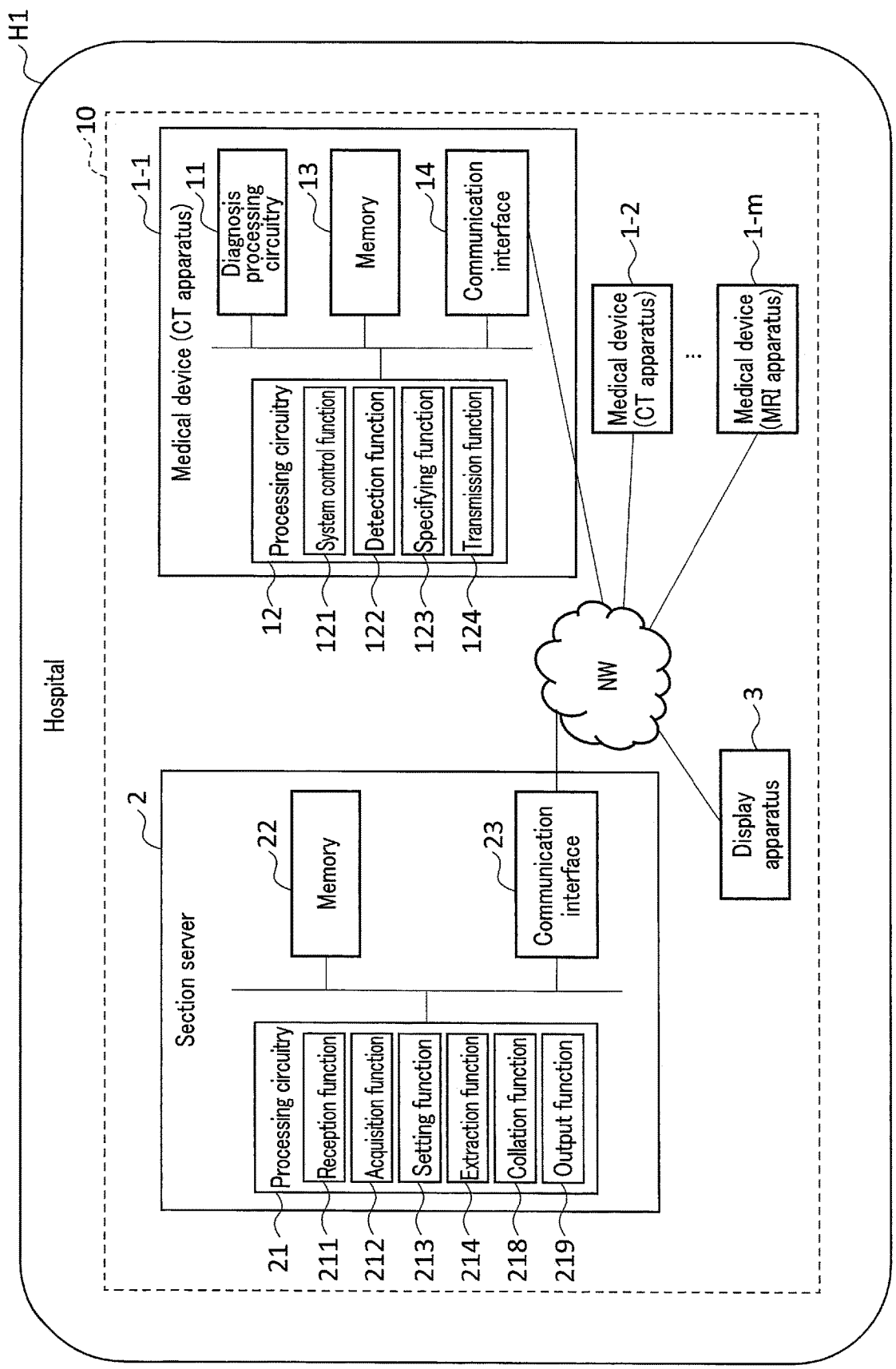
FIG. 8 is a diagram showing a configuration of an in-hospital system according to a third embodiment.

FIG. 8 is a diagram showing a configuration of an in-hospital system 10 according to the third embodiment.

Processing circuitry 21 of a section server 2 includes a collation function 218 and an output function 219 instead of the adjustment function 215, the transmission function 216, and the output function 217 explained in the first embodiment.

The collation function 218 collates measurement data relating to an operation of a destination device with measurement data relating to an operation of a source device. Hereinafter, the measurement data relating to the operation of the source device will be referred to as first data. The measurement data relating to the operation of the destination device will be referred to as second data. In a first collation example, the collation function 218 collates the first data at a timing of occurrence of the failure prediction of the source device with the second data at a timing of occurrence of the failure prediction of the destination device. The timing may be at a certain point in time or may be a period. The first collation example will be described later. In a second collation example, the collation function 218 searches for the second data that is similar to the first data at a timing prior to the timing of occurrence of the failure prediction of the destination device. Hereinafter, the timing prior to the timing of occurrence of the failure prediction of the source device will be referred to as a reference timing. The collation function 218 determines the presence or absence of the failure prediction at the destination device in accordance with the search result. The second collation example will be described later.

The output function 219 outputs a collation result obtained by the collation function 218. The collation result will be described later.

The first collation example will be explained.

Figure 9:
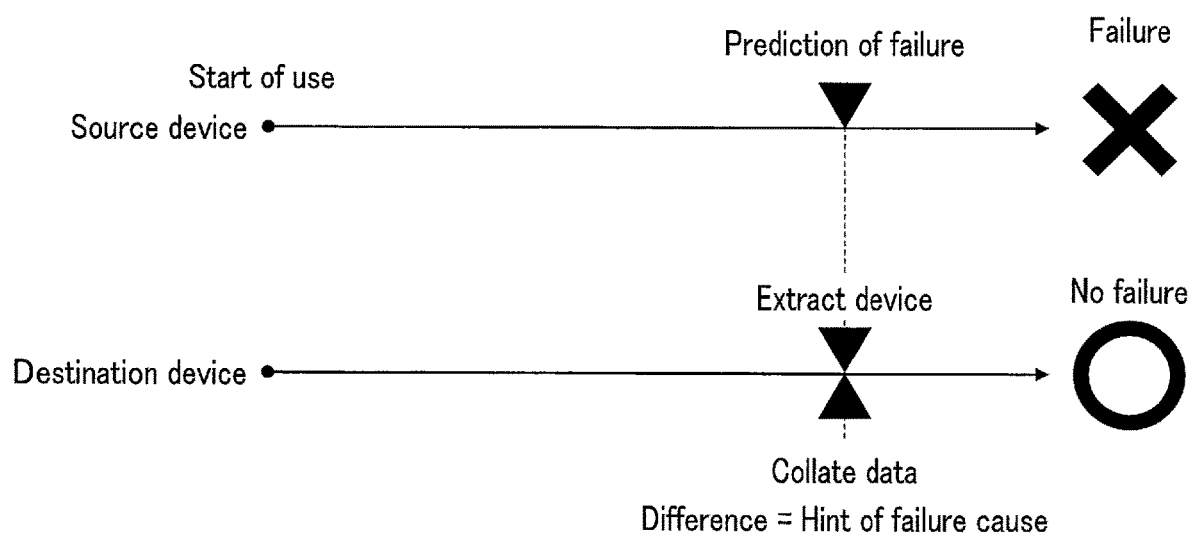
FIG. 9 is a diagram showing an example of collation processing performed by processing circuitry of a server shown in FIG. 8.

FIG. 9 is a diagram showing an example of collation processing performed by the collation function 218.

It is assumed that, by an extraction function 214, the processing circuitry 21 has extracted the destination device based on the acquisition of information indicating a failure estimation portion of the source device. The source device is assumed to have actually failed after the occurrence of the failure prediction. It is assumed that the destination device has not failed at the timing at which the source device has failed. The destination device and the source device are assumed to have started being used at the same timing; however, they may also start being used at different timings.

For example, after the source device has failed, the collation function 218 collates the first data at a timing of occurrence of the failure prediction of the source device with the second data at a timing of occurrence of the failure prediction of the source device.

A difference between the first data at a timing of occurrence of the failure prediction of the failure estimation portion and the second data at a timing of occurrence of the failure prediction of the failure estimation portion may become a hint to a specific cause of failure of the source device. One of the reasons is that the destination device is a device that is highly relevant and similar to the source device.

The collation function 218 may determine data indicating the difference between the first data and the second data as the collation result. The collation function 218 may estimate a specific cause of failure of the source device based on the difference between the first data and the second data, and determine the estimated cause of failure as the collation result.

In the first collation example, the processing circuitry 21 may transmit a request for the first data to the source device, and acquire the first data at a timing of occurrence of the failure prediction from the source device. Instead of this, the processing circuitry 21 may be configured to store the first data intermittently transmitted from the source device in a memory 22, and acquire the first data at a timing of occurrence of the failure prediction from the memory 22. Similarly, the processing circuitry 21 may transmit a request for the second data to the destination device, and acquire the second data at a timing of occurrence of the failure prediction of the source device from the destination device. Instead of this, the processing circuitry 21 may store the second data intermittently transmitted from the destination device in the memory 22, and acquire the second data at a timing of occurrence of the failure prediction of the source device from the memory 22.

According to the first collation example, the section server 2 is able to support the estimation of the cause of failure of the destination device. Furthermore, the section server 2 is able to reduce the processing load by narrowing down the device to be compared with the source device to the destination device.

The second collation example will be explained.

Figure 10:
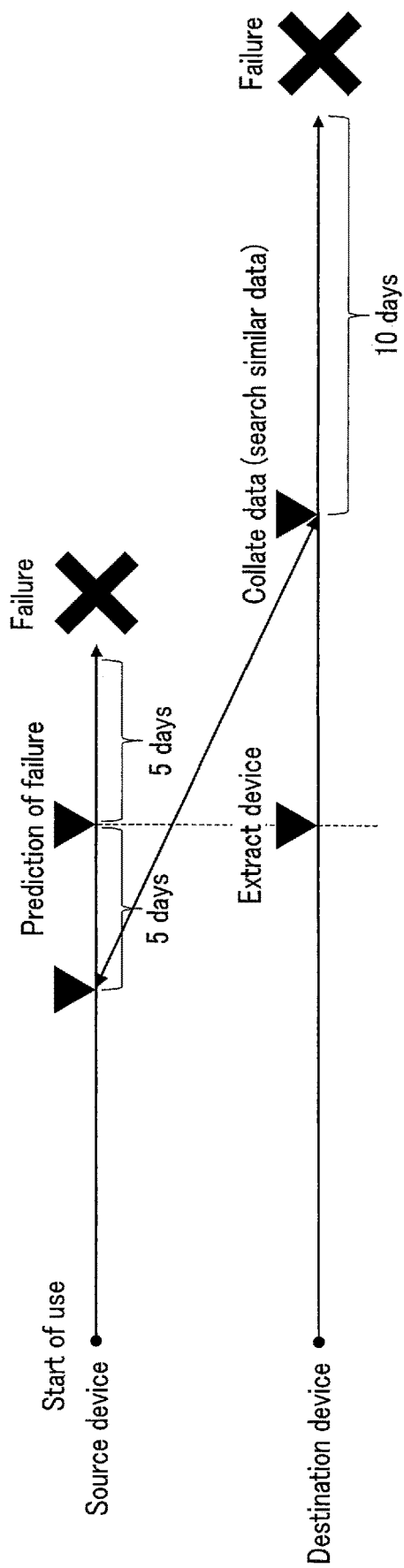
FIG. 10 is a diagram showing an example of the collation processing performed by the processing circuitry of the server shown in FIG. 8.

FIG. 10 is a diagram showing an example of the collation processing performed by the collation function 218.

It is assumed that, by the extraction function 214, the processing circuitry 21 has extracted the destination device based on acquisition of information indicating the failure estimation portion of the source device. The source device is assumed to have actually failed after five days of the occurrence of the failure prediction. The destination device and the source device are assumed to have started being used at the same timing; however, they may also start being used at different timings.

For example, after the occurrence of the failure prediction of the source device, the collation function 218 collates the first data at a reference timing with the second data at a timing after the occurrence of the failure prediction of the source device. The collation function 218 searches for the second data that is similar to the first data at the reference timing. The range of similarity may be set as appropriate. Here, the reference timing is a timing five days prior to the timing of occurrence of the failure prediction of the source device. The reference timing may be changed as appropriate. One of the reasons for conducting the search is because there is a high probability that, if a trend similar to the first data is found in the second data at the reference timing, the destination device may fail in the same manner as the source device in the future. By searching for the second data that is similar to the first data at the reference timing, the collation function 218 is able to detect the failure prediction earlier than the destination device detects the failure prediction.

The collation function 218 determines the presence or absence of the failure prediction at the destination device in accordance with the search result. In a case where the second data that is similar to the first data cannot be found at the reference timing, the collation function 218 determines that there is no failure prediction for the destination device. The collation function 218 continuously searches for the second data that is similar to the first data at the reference timing in accordance with the lapse of time. On the other hand, in a case where the second data that is similar to the first data is found at the reference timing, the collation function 218 determines that there is a failure prediction for the destination device.

The collation function 218 is assumed to have searched for the second data that is similar to the first data at a timing five days prior to the timing of occurrence of the failure prediction of the source device. The collation function 218 is able to detect the failure prediction of the destination device five days prior to the day on which it is highly possible that the destination device would detect a similar failure prediction as the source device. That is, the collation function 218 is able to detect the failure prediction of the destination device 10 days prior to the day on which there is a high probability that the destination device may actually fail.

The collation function 218 may determine the presence or absence of the failure prediction at the destination device as the collation result. The collation function 218 may also determine the day on which the failure prediction is detected at the destination device as the collation result.

In the second collation example, the processing circuitry 21 may transmit a request for the first data to the source device, and acquire the first data at the reference timing. Instead of this, the processing circuitry 21 may store the first data intermittently transmitted from the source device in the memory 22, and acquire the first data at the reference timing from the memory 22. Similarly, the processing circuitry 21 may transmit a request for the second data to the destination device, and acquire the second data for a necessary period. Instead of this, the processing circuitry 21 may store the second data intermittently transmitted from the destination device in the memory 22, and acquire the second data of the necessary period from the memory 22.

According to the second collation example, the section server 2 is able to improve the probability of detecting the failure prediction of the destination device at an early stage. Furthermore, the section server 2 is able to reduce the processing load by narrowing down the device to be compared with the source device to the destination device.

Hereinafter, processing of the section server 2 will be explained in detail.

FIG. 11 is a diagram showing an example of a flow of the collation processing performed by the processing circuitry 21 of the section server 2. The order of processing may be changed, and a part of the processing may be omitted, as appropriate.

Here, the medical device 1-1 is assumed to be the source device. The medical device 1-2 is assumed to be the destination device.

By a reception function 211, the processing circuitry 21 receives maintenance data from the medical device 1-1, which is the source device, via the communication interface 23 (step S21).

By an acquisition function 212, the processing circuitry 21 acquires information indicating a failure estimation portion of the medical device 1-1 from the maintenance data (step S22).

By a setting function 213, the processing circuitry 21 sets an extraction condition based on the failure estimation portion of the medical device 1-1 (step S23). In step S23, the processing circuitry 21 may refer to the above-mentioned extraction item management table and set the extraction condition.

By an extraction function 214, the processing circuitry 21 extracts the medical device 1-2 as the destination device under the extraction condition (step S24).

By the collation function 218, the processing circuitry 21 collates the first data with the second data (step S25). In step S25, in one example, in the manner mentioned above, the processing circuitry 21 collates the first data at a timing of occurrence of the failure prediction of the source device with the second data at a timing of occurrence of the failure prediction of the source device. In another example, the processing circuitry 21 searches for the second data that is similar to the first data at the reference timing.

By the output function 219, the processing circuitry 21 outputs a collation result obtained by the collation function 218 to a display apparatus 3 (step S26). In this manner, the display apparatus 3 displays the collation result. In step S26, the processing circuitry 21 may output the collation result to an output apparatus other than the display apparatus 3, such as a printer.

According to the third embodiment, the section server 2 is able to analyze the state of the source device or the destination device by collating the first data of the source device and the second data of the destination device.

Fourth Embodiment

Hereinafter, a fourth embodiment will be explained with reference to the drawings.

The fourth embodiment collates measurement data relating to an operation of a source device with measurement data relating to an operation of a destination device. The fourth embodiment is different from the third embodiment in that it is an example of the source device and the destination device being in different hospitals.

For configurations that are the same as those of the second embodiment, the same symbols will be used, and the explanations thereof will be omitted. In the fourth embodiment, portions different from those of the first embodiment will be mainly explained.

Figure 12:
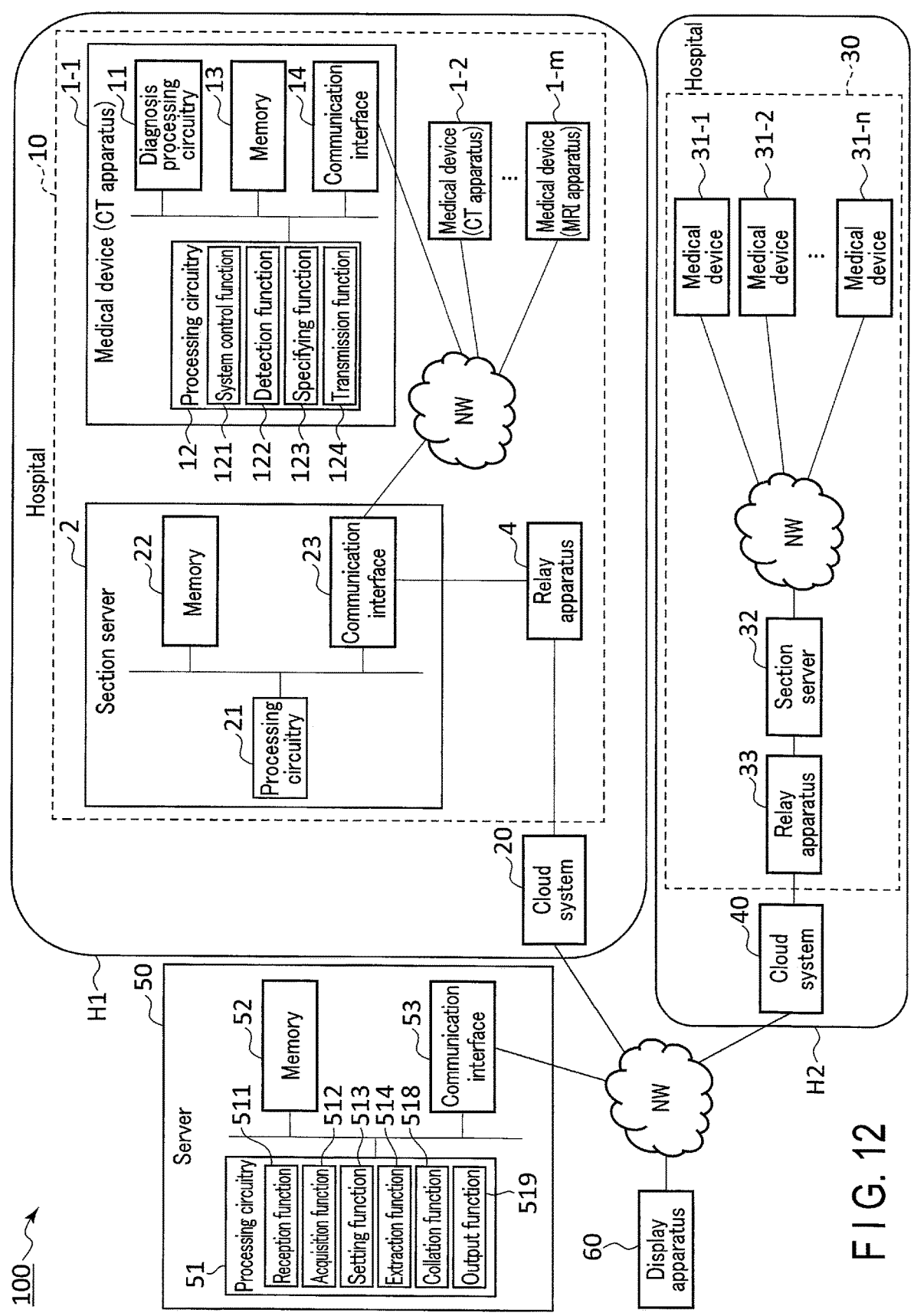
FIG. 12 is a diagram showing a configuration of an information management system according to a fourth embodiment.

FIG. 12 is a diagram showing a configuration of an in-hospital system 10 according to the fourth embodiment.

Processing circuitry 51 of a section server 50 includes a collation function 518 and an output function 519 instead of the adjustment function 515, the transmission function 516, and the output function 517 explained in the second embodiment.

The collation function 518 is the same as the collation function 218. The collation function 518 is able to collate measurement data relating to an operation of a source device with measurement data relating to an operation of a destination device belonging to a hospital different from a hospital to which the source device belongs.

The output function 519 is the same as the output function 219. The output function 519 is able to output a collation result to a display apparatus 60.

According to the fourth embodiment, the server 50 is able to analyze the state of the source device or the destination device by collating first data of the source device with second data of the destination device belonging to a different hospital from the hospital to which the source device belongs.

The third embodiment and the fourth embodiment may be configured in the following manner.

[1] A device management apparatus comprising processing circuitry configured to acquire information indicating a failure estimation portion of a first device, set an extraction condition for extracting one or more second devices based on the failure estimation portion, extract the second device by the set extraction condition, collate first data relating to an operation of the first device with second data relating to an operation of the second device, and output a collation result.

[2] The device management apparatus according to [1], wherein the processing circuitry collates the first data with the second data at a timing of occurrence of a failure prediction of the first device.

[3] The device management apparatus according to [1] or [2], wherein the processing circuitry searches for the second data that is similar to the first data at a timing prior to a timing of occurrence of a failure prediction of the first device, and determines the presence or absence of a failure prediction at the second device in accordance with a search result.

The term "processor" used in the above explanation indicates, for example, a circuit, such as a CPU, a GPU, or an application specific integrated circuit (ASIC), and a programmable logic device (for example, a simple programmable logic device (SPLD), a complex programmable logic device (CPLD), and a field programmable gate array (FPGA)). The processor reads and executes a program stored in storage circuitry to realize the functions thereof. Instead of storing a program in the storage circuitry, the program may be directly incorporated into a circuit of the processor. In this case, the processor reads and executes the program integrated into the circuit, thereby realizing its functions. The functions corresponding to the program may be realized by a combination of logic circuits, and not by executing the program. Each processor of the present embodiment is not limited to a configuration as a single circuit; a plurality of independent circuits may be combined into one processor to realize the functions of the processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A device management apparatus, comprising:
   processing circuitry configured to:
   acquire information indicating occurrence of a first failure prediction of a first medical device related to a failure estimation portion of the first medical device; and
   adjust detection sensitivity of a second failure prediction of a second medical device relating to the acquired information based on relevance between the first medical device and the second medical device by transmitting, to the second medical device, training data that was used to determine the failure estimation portion by the first medical device, the second medical device being different from the first medical device, and the second medical device applying the training data to train a machine-learning model to perform the second failure prediction of the second medical device.

2. The device management apparatus according to claim 1, wherein the processing circuitry is further configured to
   acquire information indicating the failure estimation portion of the first medical device,
   set an extraction condition for determining the second medical device based on the failure estimation portion, and
   determine the second medical device by the set extraction condition.

3. The device management apparatus according to claim 2, wherein the processing circuitry is further configured to set a different extraction condition according to the failure estimation portion.

4. The device management apparatus according to claim 3, wherein the processing circuitry is further configured to set the different extraction condition in consideration of an operation status of the first medical device.

5. The device management apparatus according to claim 2, wherein the processing circuitry is further configured to adjust the detection sensitivity of the second failure prediction for a portion of the second medical device corresponding to the failure estimation portion.

6. The device management apparatus according to claim 5, wherein the processing circuitry is further configured to determine that it is necessary to adjust the detection sensitivity of the second failure prediction according to the failure estimation portion.

7. The device management apparatus according to claim 5, wherein the processing circuitry is further configured to determine that it is necessary to adjust the detection sensitivity of the second failure prediction based on an estimation cause of the failure estimation portion.

8. A device management system, comprising:
   a device management apparatus comprising processing circuitry configured to:
   acquire information indicating occurrence of a first failure prediction of a first medical device related to a failure estimation portion of the first medical device; and
   adjust detection sensitivity of a second failure prediction of a second medical device relating to the acquired information based on relevance between the first medical device and the second medical device by transmitting, to the second medical device, training data that was used to determine the failure estimation portion by the first medical device, the second medical device being different from the first medical device, and the second medical device applying the training data to train a machine-learning model to perform the second failure prediction of the second medical device; and
   an output apparatus configured to output information relating to the first failure prediction that occurred with respect to the first medical device.

9. A device management method, comprising:
   acquiring information indicating occurrence of a first failure prediction of a first medical device related to a failure estimation portion of the first medical device; and
   adjusting detection sensitivity of a second failure prediction of a second medical device relating to the acquired information based on relevance between the first medical device and the second medical device by transmitting, to the second medical device, training data that was used to determine the failure estimation portion by the first medical device, the second medical device being different from the first medical device, and the second medical device applying the training data to train a machine-learning model to perform the second failure prediction of the second medical device.

* * * * *